United States Patent
Subramanian

(10) Patent No.: US 8,262,725 B2
(45) Date of Patent: Sep. 11, 2012

(54) TRANSVALVULAR INTRAANNULAR BAND FOR VALVE REPAIR

(75) Inventor: Valavanur A. Subramanian, New York, NY (US)

(73) Assignee: Cardiovascular Technologies, LLC, Menlo Park, CA (US)

(*) Notice: Subject to any disclaimer, the term of this patent is extended or adjusted under 35 U.S.C. 154(b) by 375 days.

(21) Appl. No.: 12/104,011

(22) Filed: Apr. 16, 2008

(65) Prior Publication Data
US 2009/0264995 A1 Oct. 22, 2009

(51) Int. Cl.
*A61F 2/24* (2006.01)
(52) U.S. Cl. ............................. 623/2.36; 623/2.37
(58) Field of Classification Search ............ 623/2.1, 623/2.36–2.39, 900
See application file for complete search history.

(56) References Cited

U.S. PATENT DOCUMENTS

| | | | |
|---|---|---|---|
| 5,360,444 A | 11/1994 | Kusuhara | |
| 5,593,424 A | 1/1997 | Northrup, III | |
| 5,906,578 A | 5/1999 | Rajan et al. | |
| 6,001,127 A | 12/1999 | Schoon et al. | |
| 6,332,893 B1 | 12/2001 | Mortier et al. | |
| 6,419,695 B1* | 7/2002 | Gabbay | 623/2.36 |
| 6,626,899 B2 | 9/2003 | Houser et al. | |
| 6,726,717 B2 | 4/2004 | Alfieri et al. | |
| 6,752,813 B2 | 6/2004 | Goldfarb et al. | |
| 6,764,510 B2 | 7/2004 | Vidlund et al. | |
| 6,797,002 B2* | 9/2004 | Spence et al. | 623/2.38 |
| 6,805,710 B2 | 10/2004 | Bolling et al. | |
| 6,869,444 B2 | 3/2005 | Gabbay | |
| 6,913,608 B2 | 7/2005 | Liddicoat et al. | |
| 7,070,618 B2 | 7/2006 | Streeter | |
| 7,077,862 B2 | 7/2006 | Vidlund et al. | |
| 7,087,064 B1 | 8/2006 | Hyde | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 2002/0065554 A1 | 5/2002 | Streeter | |
| 2003/0033009 A1* | 2/2003 | Gabbay | 623/2.36 |

(Continued)

FOREIGN PATENT DOCUMENTS
EP 1 059 893 B1 9/2005
(Continued)

OTHER PUBLICATIONS

International Search Report for PCT/US2009/040386, Jun. 4, 2009.
(Continued)

*Primary Examiner* — David H. Willse
*Assistant Examiner* — Tiffany Shipmon
(74) *Attorney, Agent, or Firm* — Knobbe, Martens, Olson & Bear LLP

(57) ABSTRACT

Mitral valve prolapse and mitral regurgitation can be treating by implanting in the mitral annulus a transvalvular intraannular band having an elongate and arcuate body. The elongate and arcuate body has a first end, a first anchoring portion located proximate the first end, a second end, a second anchoring portion located proximate the second end, and a central portion. The central portion is displaced from the plane containing the first end and the second end. The transvalvular band is positioned so that it extends transversely across a coaptive edge formed by the closure of the mitral valve leaflets and the central portion is displaced towards the left ventricle relative to the first anchoring portion and the second anchoring portion. The ventricular direction displacement moves coaption to an earlier point in the cardiac cycle.

21 Claims, 16 Drawing Sheets

U.S. PATENT DOCUMENTS

| | | | |
|---|---|---|---|
| 2003/0083742 A1* | 5/2003 | Spence et al. ............... 623/2.16 |
| 2003/0093148 A1 | 5/2003 | Bolling et al. |
| 2003/0120340 A1* | 6/2003 | Liska et al. ................... 623/2.1 |
| 2003/0199974 A1* | 10/2003 | Lee et al. ..................... 623/2.36 |
| 2004/0088047 A1* | 5/2004 | Spence et al. ............... 623/2.36 |
| 2004/0106989 A1 | 6/2004 | Wilson et al. |
| 2004/0127982 A1 | 7/2004 | Machold et al. |
| 2004/0138745 A1 | 7/2004 | Macoviak et al. |
| 2004/0152947 A1 | 8/2004 | Schroeder et al. |
| 2004/0162610 A1 | 8/2004 | Liska et al. |
| 2004/0225300 A1 | 11/2004 | Goldfarb et al. |
| 2004/0260393 A1 | 12/2004 | Rahdert et al. |
| 2005/0004665 A1 | 1/2005 | Aklog et al. |
| 2005/0004666 A1 | 1/2005 | Alfieri et al. |
| 2005/0004668 A1* | 1/2005 | Aklog et al. ................. 623/2.36 |
| 2005/0010287 A1 | 1/2005 | Macoviak et al. |
| 2005/0038508 A1 | 2/2005 | Gabbay |
| 2005/0070999 A1 | 3/2005 | Spence |
| 2005/0075723 A1 | 4/2005 | Schroeder et al. |
| 2005/0107871 A1* | 5/2005 | Realyvasquez et al. ..... 623/2.11 |
| 2005/0143811 A1 | 6/2005 | Realyvasquez |
| 2005/0216039 A1 | 9/2005 | Lederman |
| 2005/0256568 A1 | 11/2005 | Lim et al. |
| 2005/0267573 A9 | 12/2005 | Macoviak et al. |
| 2005/0288776 A1 | 12/2005 | Shaoulian et al. |
| 2006/0004443 A1 | 1/2006 | Liddicoat et al. |
| 2006/0020336 A1 | 1/2006 | Liddicoat |
| 2006/0058871 A1 | 3/2006 | Zakay et al. |
| 2006/0069430 A9 | 3/2006 | Rahdert et al. |
| 2006/0106456 A9 | 5/2006 | Machold et al. |
| 2006/0149368 A1* | 7/2006 | Spence ........................ 623/2.37 |
| 2006/0161040 A1 | 7/2006 | McCarthy et al. |
| 2006/0195012 A1 | 8/2006 | Mortier et al. |
| 2006/0229708 A1 | 10/2006 | Powell et al. |
| 2006/0247492 A1 | 11/2006 | Streeter |
| 2008/0243245 A1 | 10/2008 | Thambar et al. |
| 2009/0264995 A1 | 10/2009 | Subramanian |

FOREIGN PATENT DOCUMENTS

| | | | |
|---|---|---|---|
| WO | WO98/18411 | * | 7/1998 |
| WO | WO 00/60995 | | 10/2000 |

OTHER PUBLICATIONS

U.S. Appl. No. 12/579,330, filed Oct. 14, 2009, Subramanian et al.
U.S. Appl. No. 12/579,331, filed Oct. 14, 2009, Subramanian et al.
U.S. Appl. No. 12/579,364, filed Oct. 14, 2009, Subramanian et al.
Office Action for App. No. 12/626,272 mailed Apr. 29, 2010 in 7 pages.
International Search Report and Written Opinion for PCT/US2010/052695 mailed Dec. 6, 2010 in 18 pages.

* cited by examiner

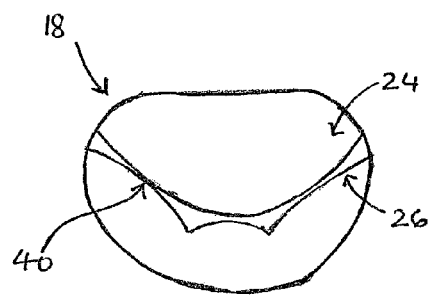
FIG. 3
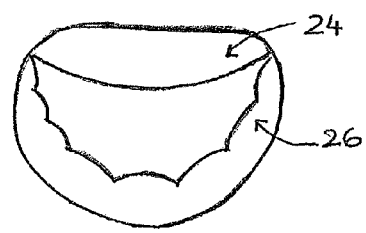
FIG. 5
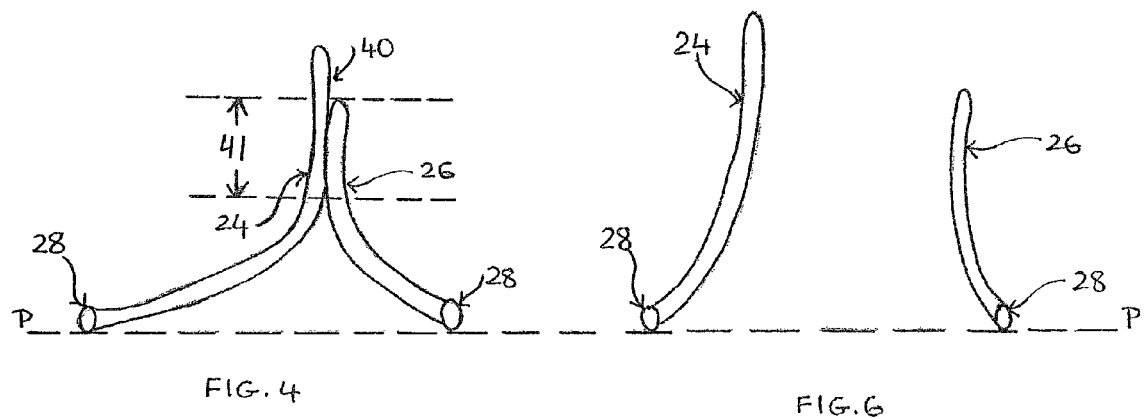
FIG. 4
FIG. 6

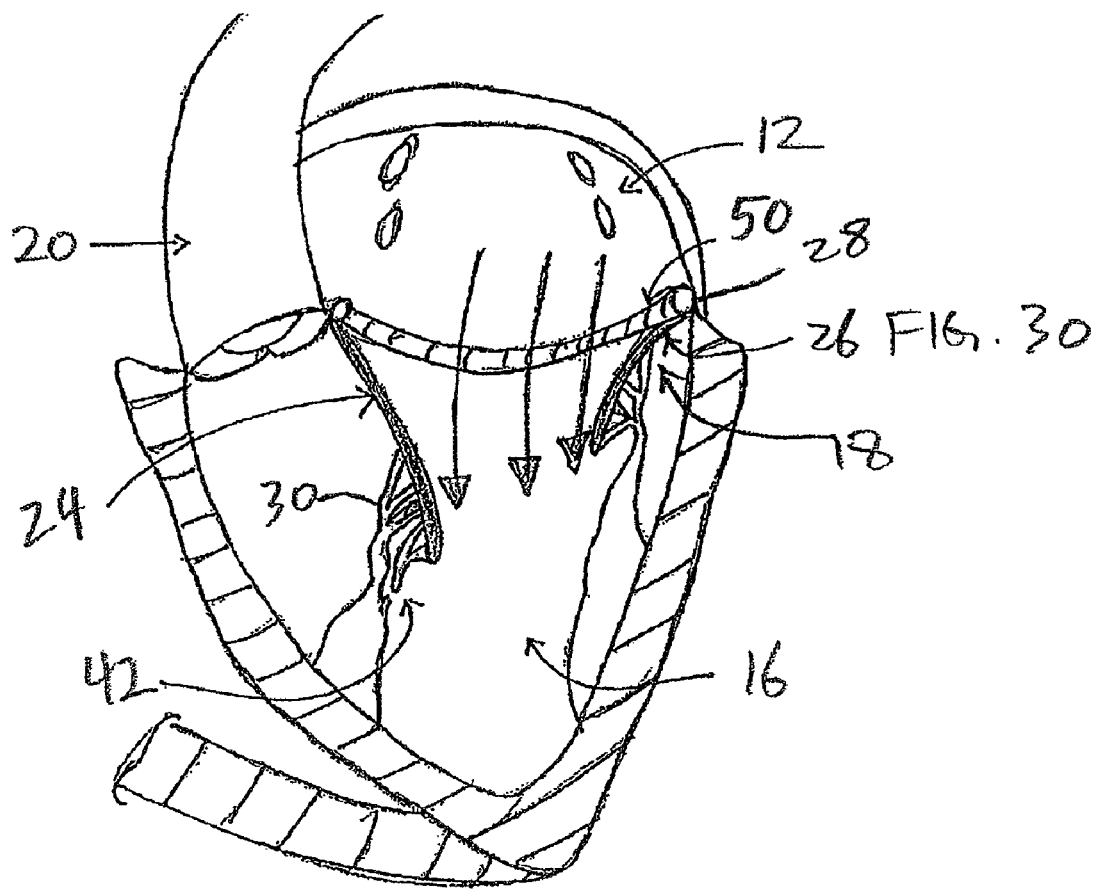
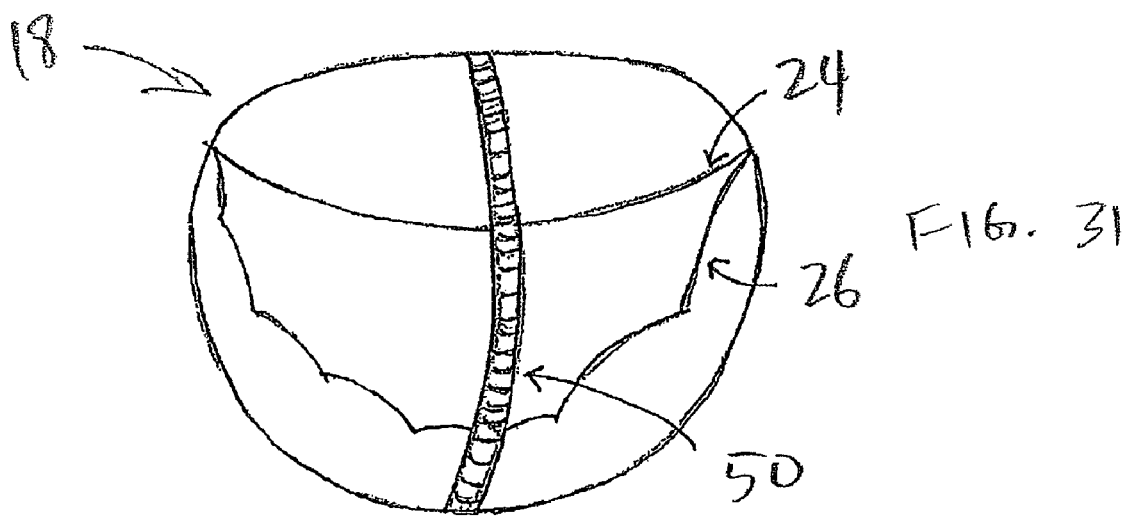

TRANSVALVULAR INTRAANNULAR BAND FOR VALVE REPAIR

BACKGROUND OF THE INVENTION

1. Field of the Invention

Embodiments of the present invention relate generally to treatment of mitral or tricuspid valve prolapse and mitral regurgitation, and more specifically, relate to the use of a transannular band to treat mitral valve prolapse and mitral regurgitation.

2. Description of the Related Art

The heart is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenated ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

Various disease processes can impair the proper functioning of one or more of these valves. These include degenerative processes (e.g., Barlow's Disease, fibroelastic deficiency), inflammatory processes (e.g., Rheumatic Heart Disease) and infectious processes (e.g., endocarditis). In addition, damage to the ventricle from prior heart attacks (i.e., myocardial infarction secondary to coronary artery disease) or other heart diseases (e.g., cardiomyopathy) can distort the valve's geometry causing it to dysfunction.

The mitral valve is comprised of an anterior leaflet and a posterior leaflet. The bases of the leaflets are fixed to a circumferential partly fibrous structure, the annulus, preventing dehiscence of the valve. A subvalvular apparatus of chordae and papillary muscles prevents the valve from prolapsing into the left atrium. Mitral valve disease can be expressed as a complex variety of pathological lesions of either valve or subvalvular structures, but can also be related to the functional status of the valve. Functionally the mitral valve disease can be categorized into two anomalies, increased leaflet motion i.e. leaflet prolapse leading to regurgitation, or diminished leaflet motion i.e. restricted leaflet motion leading to obstruction and/or regurgitation of blood flow.

Leaflet prolapse is defined as when a portion of the leaflet overrides the plane of the orifice during ventricular contraction. The mitral regurgitation can also develop secondary to alteration in the annular ventricular apparatus and altered ventricular geometry, followed by incomplete leaflet coaptation. In ischemic heart failure this can be attributed to papillary or lateral wall muscle dysfunction, and in non-ischemic heart failure it can be ascribed to annular dilation and chordal tethering, all as a result of dysfunctional remodeling.

The predominant cause of dysfunction of the mitral valve is regurgitation which produces an ineffective cardiac pump function resulting in several deleterious conditions such as ventricular and atrial enlargement, pulmonary hypertension and heart-failure and ultimately death.

The main objective for the surgical correction is to restore normal function and not necessarily anatomical correction. This is accomplished by replacing the valve or by reconstructing the valve. Both of the procedures require the use of cardiopulmonary bypass and is a major surgical operation carrying a non-negligible early morbidity and mortality risk, and a postoperative rehabilitation for months with substantial postoperative pain. Historically, the surgical approach to patients with functional mitral regurgitation was mitral valve replacement, however with certain adverse consequences such as thromboembolic complications, the need for anticoagulation, insufficient durability of the valve, loss of ventricular function and geometry.

Reconstruction of the mitral valve is therefore the preferred treatment for the correction of mitral valve regurgitation and typically consists of a quadrangular resection of the posterior valve (valvuloplasty) in combination with a reduction of the mitral valve annulus (annuloplasty) by the means of suturing a ring onto the annulus. These procedures are surgically demanding and require a bloodless and well-exposed operating field for an optimal surgical result. The technique has virtually not been changed for more than three decades.

More recently, prolapse of the valve has been repaired by anchoring the free edge of the prolapsing leaflet to the corresponding free edge of the opposing leaflet and thereby restoring apposition but not necessarily coaptation. In this procedure a ring annuloplasty is also required to attain complete coaptation.

This method commonly referred to as an edge-to-edge or "Alfieri" repair also has certain drawbacks such as the creation of a double orifice valve and thereby reducing the effective orifice area. Several less invasive approaches related to the edge-to-edge technique has been suggested, for repairing mitral valve regurgitation by placing a clip through a catheter to suture the valve edges. However, it still remains to conduct an annuloplasty procedure, which has not yet been resolved by a catheter technique and therefore is to be performed by conventional surgery, which makes the method impractical.

Notwithstanding the presence of a variety of presently available surgical techniques and promising catheter based procedures for the future, there remains a need for a simple but effective device and corresponding surgical, minimally invasive or transvascular procedure to reduce mitral valve regurgitation.

SUMMARY OF THE INVENTION

There is provided in accordance with aspect of the present invention, a transannular band for improving cardiac function. The band comprises an elongate and arcuate body, having a first end, a first anchoring portion located near the first end, and a second end, having a second anchoring portion located near the second end. A central portion is provided, for spanning the flow path of a valve such as a mitral valve. The central portion is displaced transversally from a plane which includes the first end and second end. As implanted, the transverse displacement advances the coaption point of the closed valve in the direction of the ventricle. The first end and second end are configured to be attached to opposing sides of a mitral valve annulus, and the central portion is configured to support the mitral valve leaflets.

In one embodiment, the central portion is narrower than both the first anchoring portion and the second anchoring portion, measured in a transverse direction to blood flow.

In accordance with another aspect of the present invention, there is provided a method of treating valve prolapse. In one implementation of the invention, the method is optimized for treating mitral valve prolapse.

The method comprises the steps of implanting in the mitral valve annulus a transannular band comprising an elongate and arcuate body, having a first end, a first anchoring portion located proximate the first end, and a second end, having a second anchoring portion located proximate the second end. A central portion is provided, for spanning the blood flow path. The central portion is displaced from a plane which includes the first end and the second end.

The first anchoring portion is attached to a first portion of the mitral annulus, and the second anchoring portion is attached to a second portion of the mitral annulus, such that the transannular band extends transversely across a coaptive edge formed by the closure of the mitral valve leaflets. The transannular band is implanted such that the central portion is displaced in the direction of the left ventricle relative to the first anchoring portion and the second anchoring portion.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a bottom view of the normal mitral valve of FIG. 1 during systole looking from the left atrium to the left ventricle.

FIG. 4 is a cross-sectional schematic view of the normal mitral valve of FIG. 1 during systole, illustrating the depth of the coaption zone.

FIG. 5 is a bottom view of the normal mitral valve of FIG. 2 during diastole looking from the left atrium to the left ventricle.

FIG. 6 is a cross-sectional schematic view of the normal mitral valve of FIG. 2 during diastole.

FIG. 11B is a cross sectional view as in FIG. 11, showing bileaflet prolapse with mitral regurgitation.

FIG. 11C illustrates a dilated mitral annulus with little or no coaption of both leaflets causing central mitral regurgitation in ischemic cardiomyopathy.

FIG. 30 is a cross-sectional view of a heart during diastole with mitral valve and a transannular band implanted in the mitral annulus.

FIG. 31 is a bottom view of the mitral valve of FIG. 30 during diastole with a transannular band implanted in the mitral annulus looking from the left atrium to the left ventricle.

DETAILED DESCRIPTION OF THE PREFERRED EMBODIMENT

Figure 1:
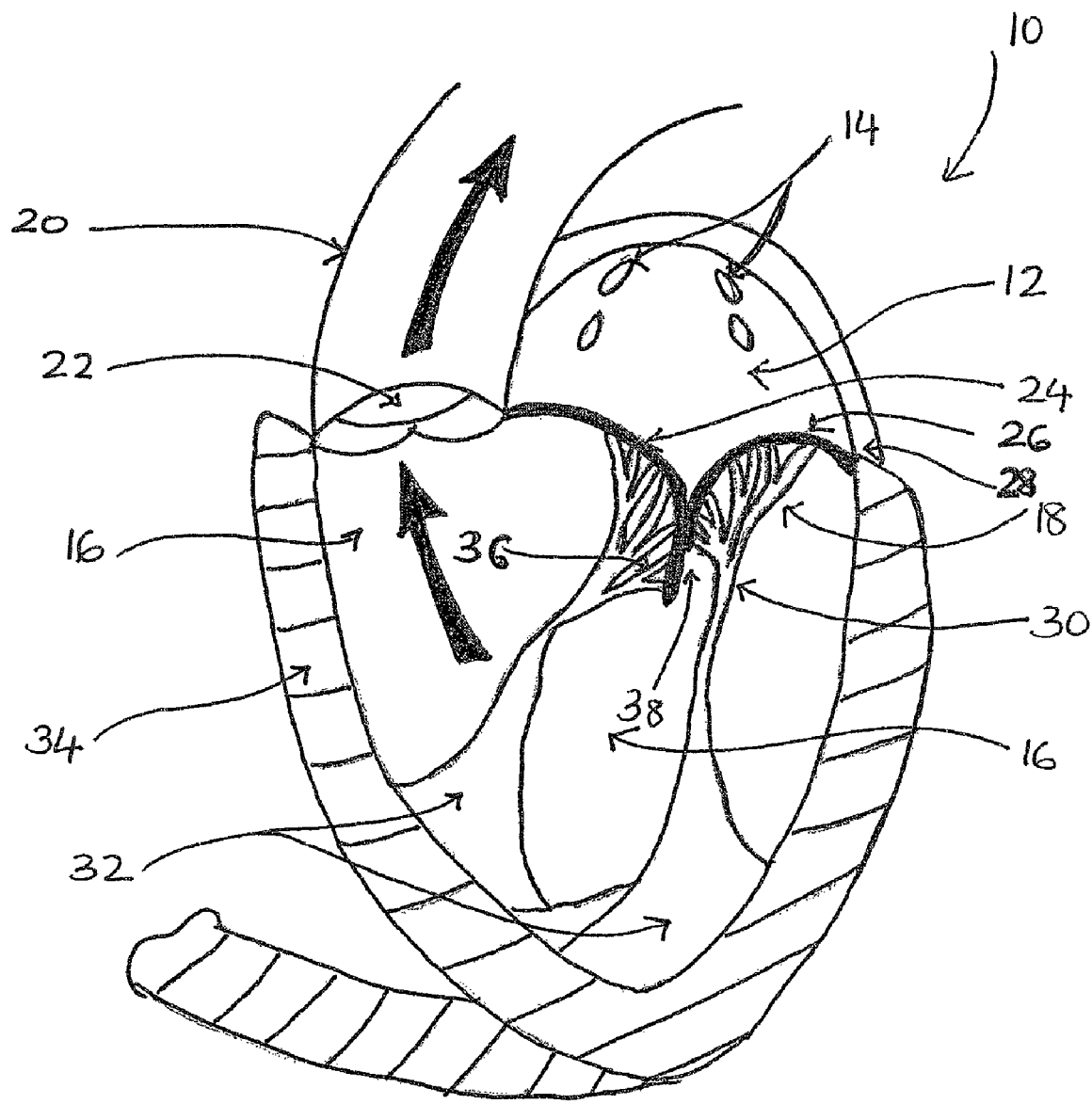
FIG. 1 is a simplified cross-sectional view of the heart with a normal mitral valve during systole.

FIG. 1 illustrates a cross-sectional view of the heart 10 with a normal mitral valve 18 in systole. As illustrated, the heart 10 comprises the left atrium 12 which receives oxygenated blood from the pulmonary veins 14 and the left ventricle 16 which receives blood from the left atrium 12. The mitral valve 18 is located between the left atrium 12 and left ventricle 16 and functions to regulate the flow of blood from the left atrium 12 to the left ventricle 16. During ventricular diastole, the mitral valve 18 is open which allows blood to fill the left ventricle 16. During ventricular systole, the left ventricle 16 contracts, which results in an increase in pressure inside the left ventricle 16. The mitral valve 18 closes when the pressure inside the left ventricle 16 increases above the pressure within the left atrium 12. The pressure within the left ventricle 16 continues increasing until the pressure within the left ventricle 16 exceeds the pressure within the aorta 20, which causes the aortic valve 22 to open and blood to be ejected from the left ventricle and into the aorta 20.

The mitral valve 18 comprises an anterior leaflet 24 and a posterior leaflet 26 that have base portions that are attached to a fibrous ring called the mitral valve annulus 28. Each of the leaflets 24 and 26 has respective free edges 36 and 38. Attached to the ventricular side of the leaflets 24 and 26 are relatively inelastic chordae tendineae 30. The chordae tendineae 30 are anchored to papillary muscles 32 that extend from the intraventricular septum 34. The chordae tendineae 30 and papillary muscle 32 function to prevent the leaflets 24 and 26 from prolapsing and enable proper coaptation of the leaflets 24 and 26 during mitral valve 18 closure.

Figure 2:
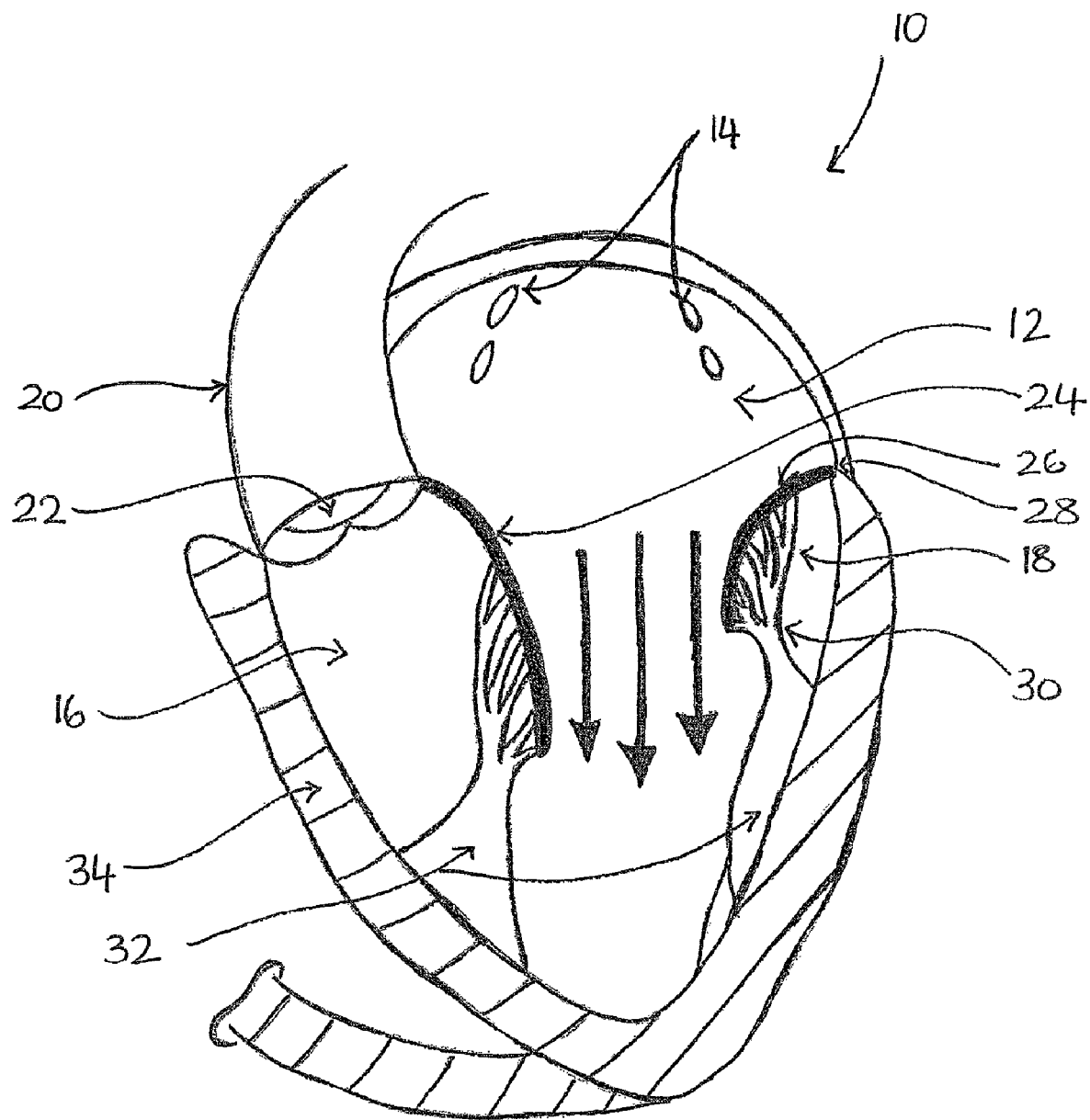
FIG. 2 is a cross-sectional view of the heart with a normal mitral valve during diastole.

FIG. 2 illustrates a cross-sectional view of the heart 10 with a normal mitral valve 18 in diastole. After the left ventricle 16 has ejected the blood into the aorta, the left ventricle relaxes, which results in a drop in pressure within the left ventricle 16. When the pressure in the left ventricle 16 drops below the pressure in the aorta 20, the aortic valve 22 closes. The pressure within the left ventricle 16 continues dropping until the pressure in the left ventricle 16 is less than the pressure in the left atrium 12, at which point the mitral valve 18 opens, as shown in FIG. 2. During the early filling phase, blood passively fills the left ventricle 16 and this accounts for most of the filling of the left ventricle 16 in an individual at rest. At the end of the filling phase, the left atrium 12 contracts and provides a final kick that ejects additional blood into the left ventricle.

FIG. 3 illustrates a bottom view of normal mitral valve 18 in systole, looking from the left atrium and to the left ventricle. As shown, the anterior leaflet 24 and posterior leaflet 26 are properly coapted, thereby forming a coaptive edge 40 that forms a seal that prevents retrograde flow of blood through the mitral valve 18, which is known as mitral regurgitation. FIG. 4 provides a side cross-sectional view of a normal mitral valve 18 in systole. As shown in FIG. 4, the valve leaflets 24 and 26 do not normally cross the plane P defined by the annulus and the free edges 36 and 38 coapt together to form a coaptive edge 40.

FIG. 4 also illustrates a coaption zone 41. Preferably the depth of coaption (length of zone 41 in the direction of blood flow, in which the leaflets 24 and 26 are in contact) is at least about 2 mm or 5 mm, and is preferably within the range of from about 7 mm to about 10 mm for the mitral valve.

Thus, implantation of the devices in accordance with the present invention preferably achieves an increase in the depth of coaption. At increase of at least about 1 mm, preferably at least about 2 mm, and in some instances an increase of at least about 3 mm to 5 mm or more may be accomplished.

Figure 19A:
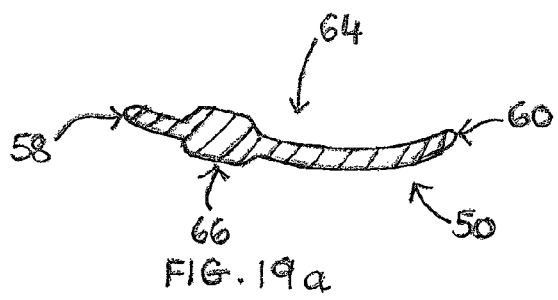
FIGS. 19A and B show a perspective view of yet another embodiment of a transannular band, with a widened coaptive edge support portion.
Figure 19B:
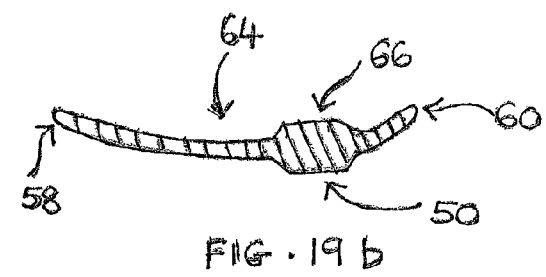

In addition to improving coaption depth, implantation of devices in accordance with the present invention preferably also increase the width of coaptation along the coaption plane. This may be accomplished, for example, by utilizing an implant having a widened portion for contacting the leaflets in the area of coaption such as is illustrated in connection with FIGS. 19A and 19B below. A further modification of the coaptive action of the leaflets which is accomplished in accordance with the present invention is to achieve early coaption. This is accomplished by the curvature or other elevation of the implant in the ventricle direction. This allows the present invention to achieve early coaption relative to the cardiac cycle, relative to the coaption point prior to implantation of devices in accordance with the present invention.

FIGS. 5 and 6 illustrate normal mitral valve 18 in diastole. As shown, the anterior leaflet 24 and posterior leaflet 26 are in a fully opened configuration which allows blood to flow from the left atrium to the left ventricle.

Figure 7:
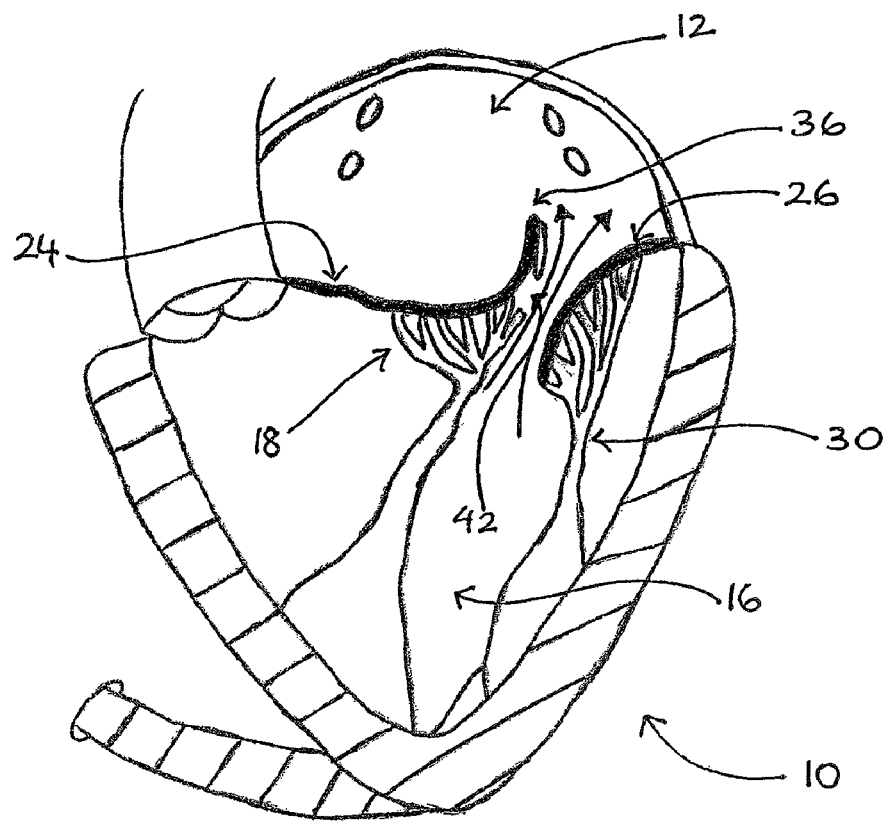
FIG. 7 is a cross-sectional view of the heart during systole showing a mitral valve with a prolapsed anterior leaflet caused by the rupture of the chordae tendineae attached to the anterior leaflet.
Figure 8:
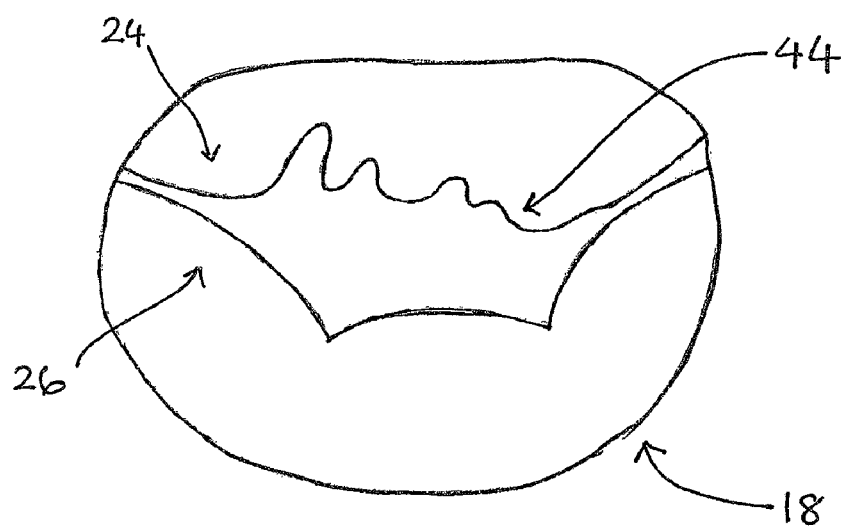
FIG. 8 is a bottom view of the mitral valve of FIG. 7 having a prolapsed anterior leaflet looking from the left atrium to the left ventricle.

FIGS. 7 and 8 illustrate a heart 10 in systole where the anterior leaflet 24 of the mitral valve 18 is in prolapse. Anterior leaflet 24 prolapse can be caused by a variety of mechanisms. For example, as illustrated in FIG. 7, rupture 42 of a portion of the chordae tendineae 30 attached to the anterior leaflet 24 can cause the free edge 36 of the anterior leaflet 24 to invert during mitral valve 18 closure. As shown in FIG. 8, inversion 44 of the anterior leaflet 24 can prevent the mitral valve leaflets 24 and 26 from properly coapting and forming a seal. This situation where the free edge 36 of the anterior leaflet 24 crosses into the left atrium 12 during mitral valve 18 closure can lead to mitral regurgitation.

Figure 9:
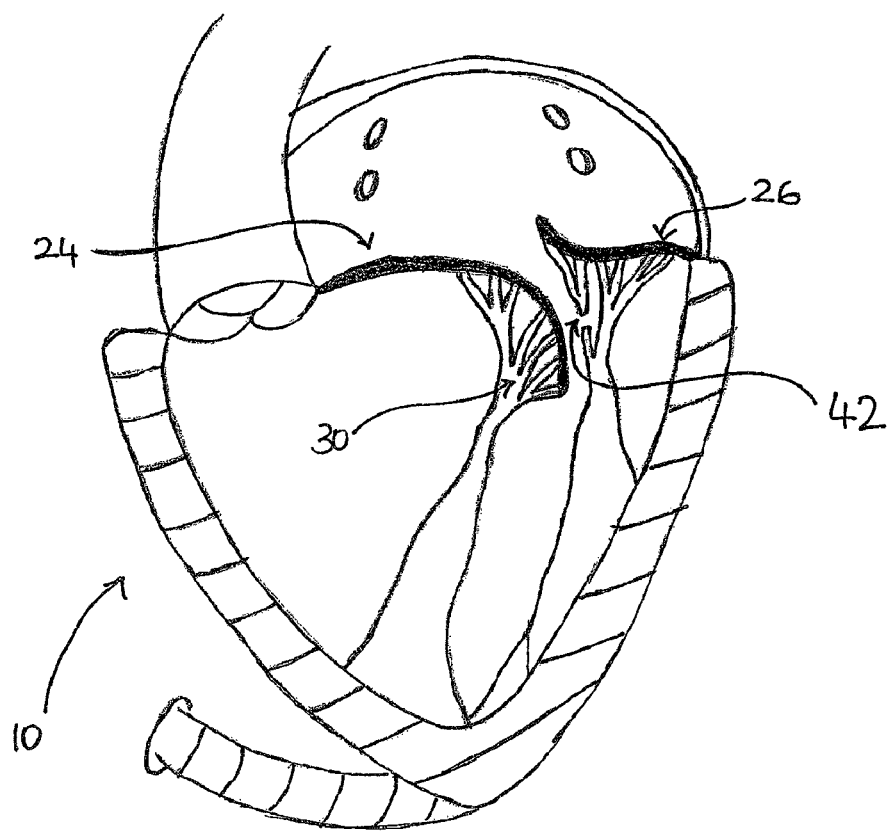
FIG. 9 is a cross-sectional view of the heart during systole showing a mitral valve with a prolapsed posterior leaflet caused by the rupture of the chordae tendineae attached to the posterior leaflet.
Figure 10:
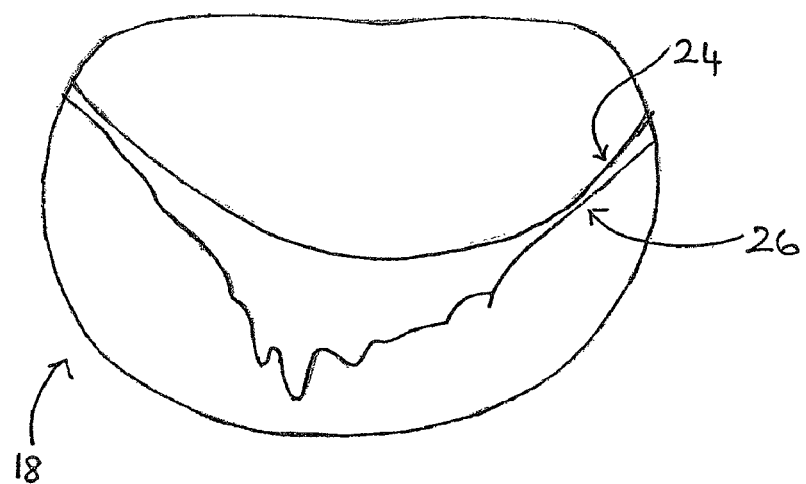
FIG. 10 is a bottom view of the mitral valve of FIG. 9 having a prolapsed posterior leaflet looking from the left atrium to the left ventricle.

Similarly, FIGS. 9 and 10 illustrate posterior leaflet 26 prolapse caused by a rupture of the chordae tendineae 30 attached to the posterior leaflet 26. In this case, the posterior leaflet 26 can invert and cross into the left atrium 12 during mitral valve 18 closure. The inversion of the posterior leaflet 26 prevents the mitral valve leaflets 24 and 26 from properly coapting and forming a seal, which can lead to mitral regurgitation.

Figure 11:
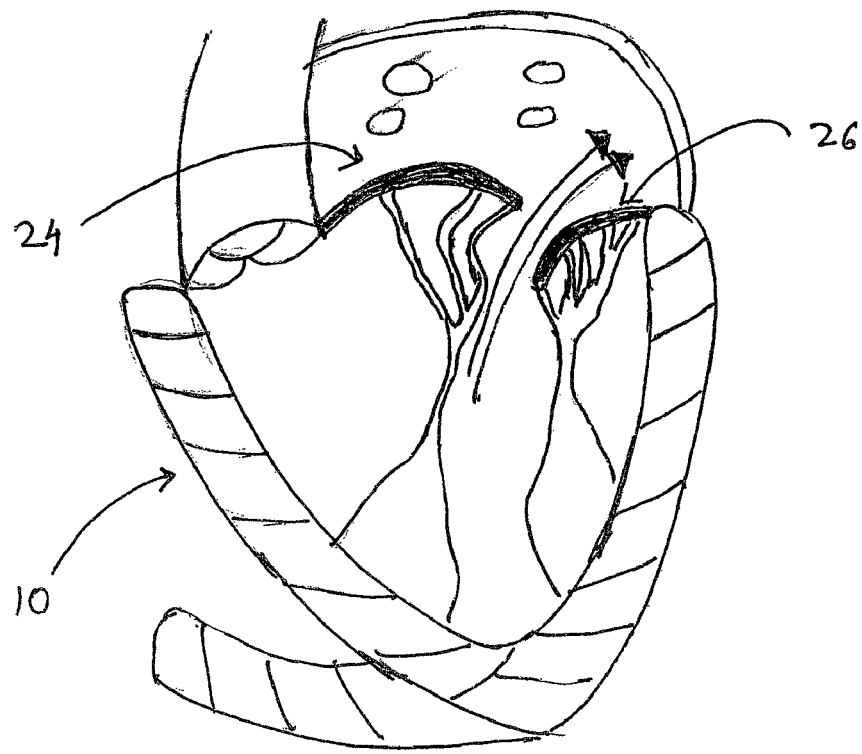
FIG. 11 is a cross-sectional view of the heart during systole showing a mitral valve with anterior leaflet prolapse.
Figure 11A:
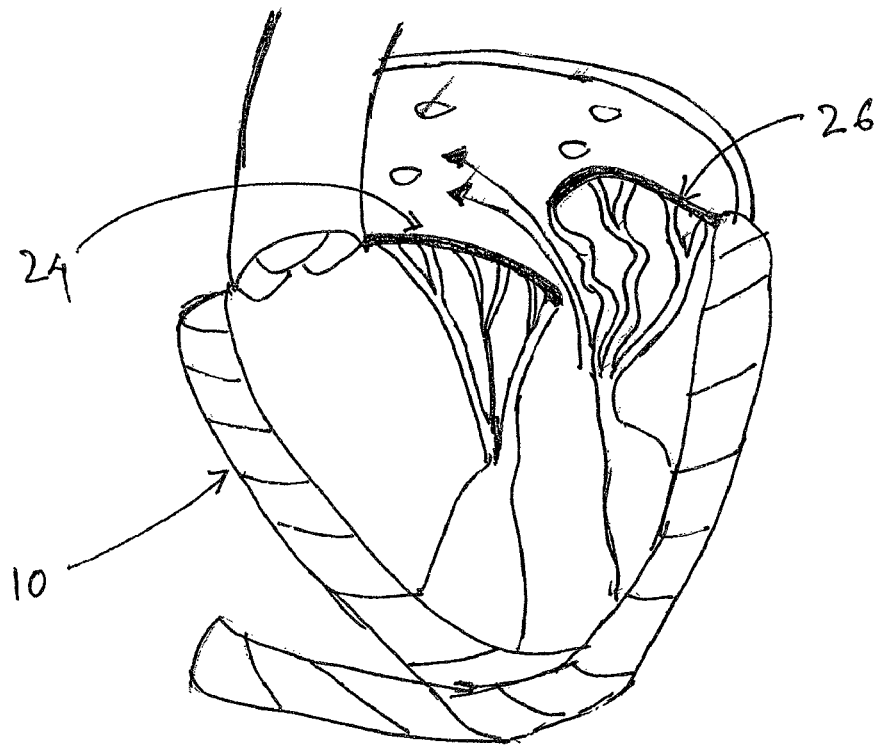
FIG. 11A is a cross sectional view as in FIG. 11, showing posterior leaflet prolapse.
Figure 11:
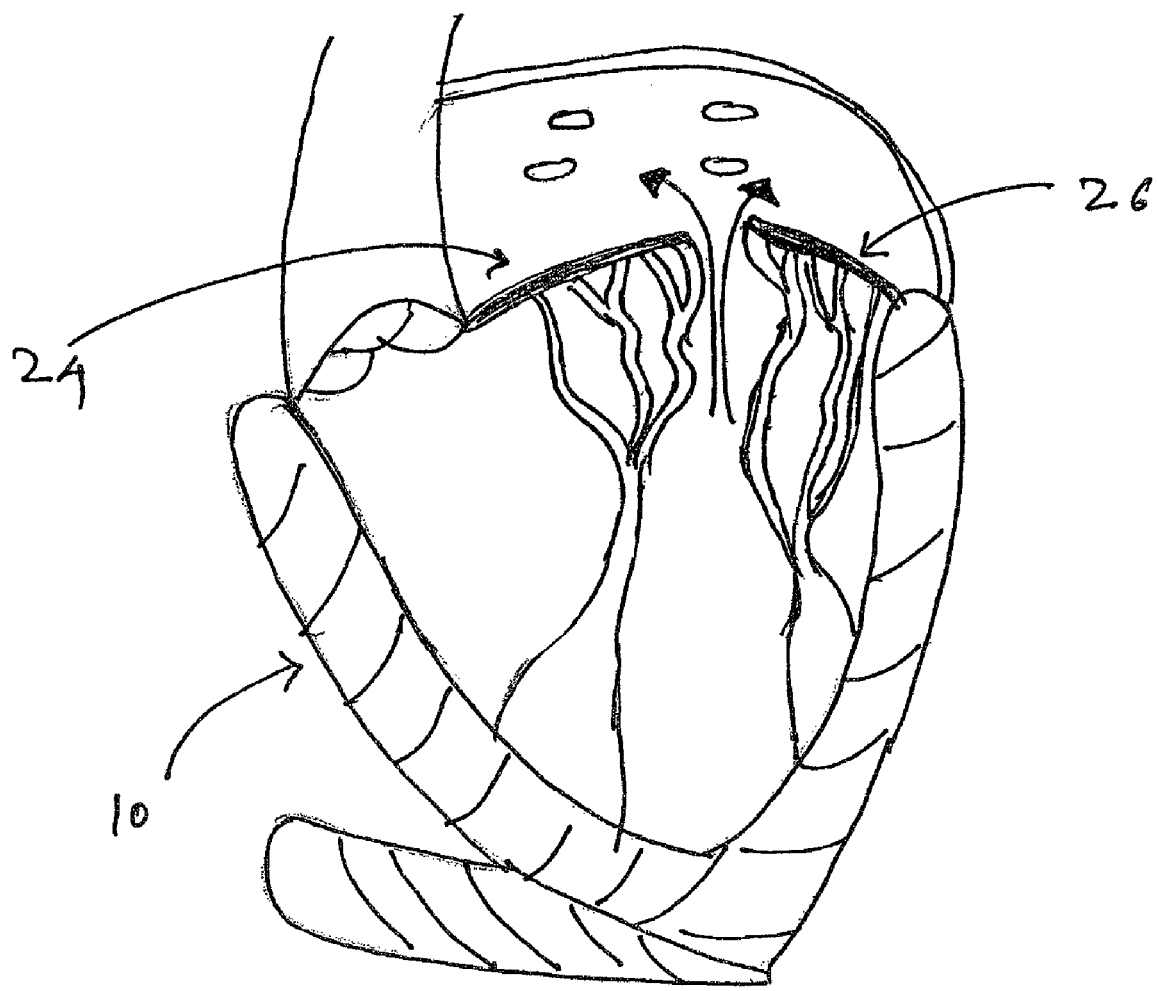
Figure 11:
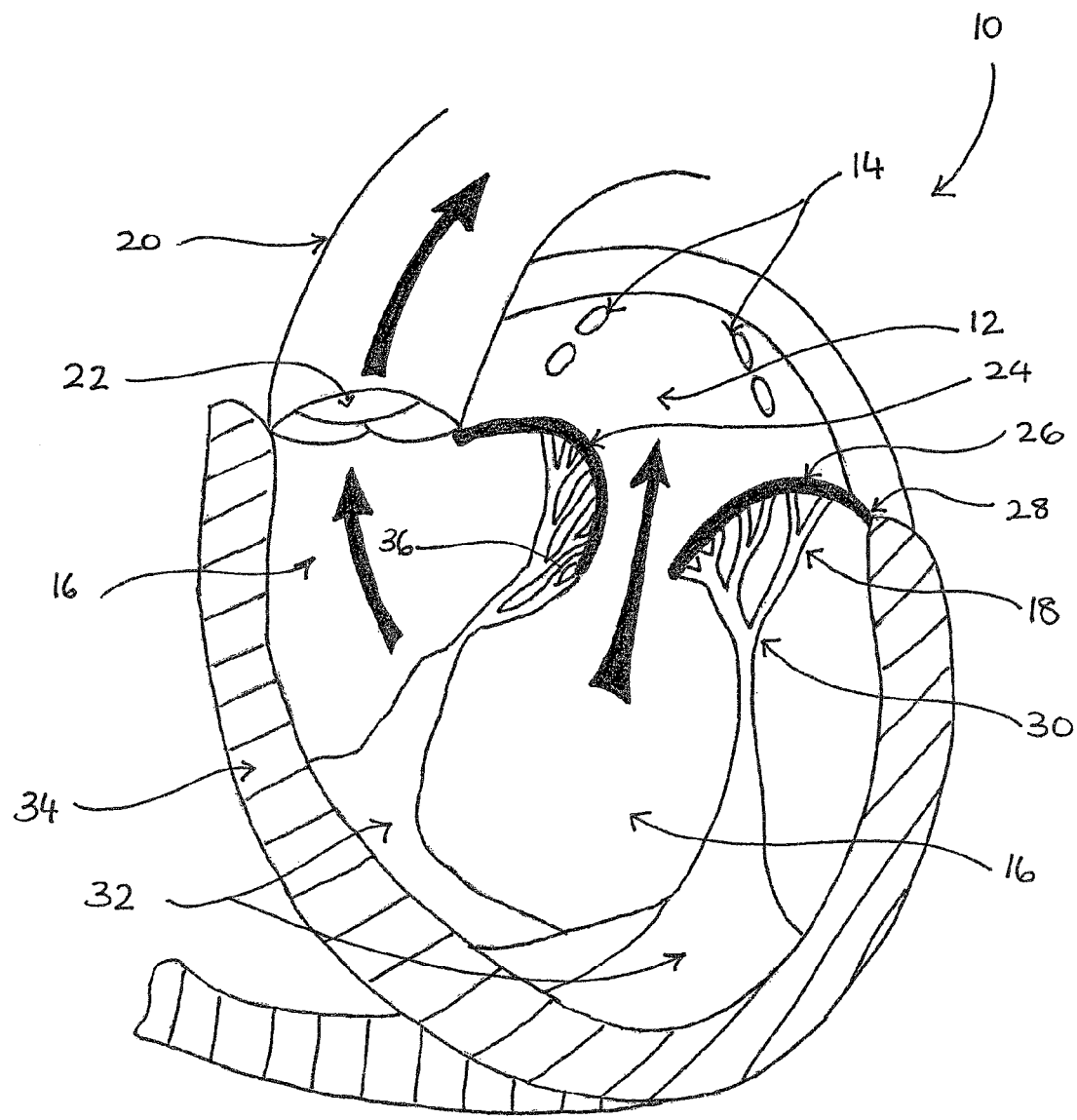

Mitral regurgitation can also be caused by an elongated valve leaflet 24 and 26. For example, an elongated anterior leaflet 24, as shown in FIG. 11, can prevent the valve leaflets 24 and 26 from properly coapting during mitral valve 18 closure. This can lead to excessive bulging of the anterior leaflet 24 into the left atrium 12 and misalignment of the free edges 36 and 38 during coaptation, which can lead to mitral regurgitation.

Figure 12:
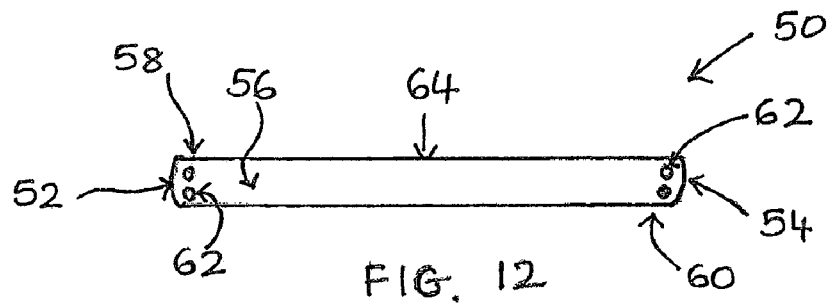
FIG. 12 is a top view of an embodiment of a transannular band.
Figure 13:
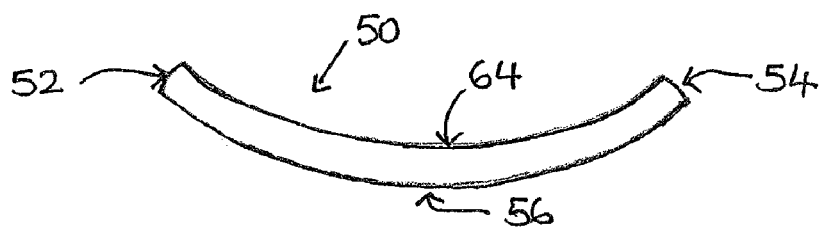
FIG. 13 is a side view of the transannular band of FIG. 12.

One embodiment of a transannular band 50 that would improve mitral valve leaflet 24 and 26 coaptation and prevent or reduce mitral regurgitation is illustrated in FIGS. 12 and 13. FIG. 12 provides a top view of the transannular band 50 while FIG. 13 provides a side view of the transannular band 50. In this embodiment, the transannular band 50 comprises an elongate and curved structure with a first end 52, a second end 54, a central portion 64 located between the two ends 52 and 54, and a length that is capable of extending across the annulus. The leaflet contact surface 56 is convex along the longitudinal axis, as best illustrated in FIG. 13. In other embodiments, the leaflet contact surface 56 can have a different shape and profile. For example, the contact surface 56 can be concave, straight, a combination of convex, concave and/or straight, or two concave or straight portions joined together at an apex. As illustrated in FIG. 12, the transannular band 50 can have a substantially constant width between the first end 52 and the second end 54. The first end 52 has a first anchoring portion 58 and the second end 54 has a second anchoring portion 60.

The anchoring portions 58 and 60 can have holes 62 for sutures that allow the transannular band 50 to be secured to the annulus. Alternatively, in other embodiments the anchoring portions 58 and 60 can have other means for securing the transannular band 50 to the annulus. For example, the anchoring portions 58 and 60 can be made of a membrane or other fabric-like material such as Dacron or ePTFE. Sutures can be threaded directly through the fabric without the need for distinct holes 62. The fabric can be attached to the other portions of the transannular band 50 by a variety of techniques. For example, the fabric can be attached to the other portions of the transannular band 50 with the use of an adhesive, by suturing, by tying, by clamping or by fusing the parts together.

Figures 14, 15, 16:
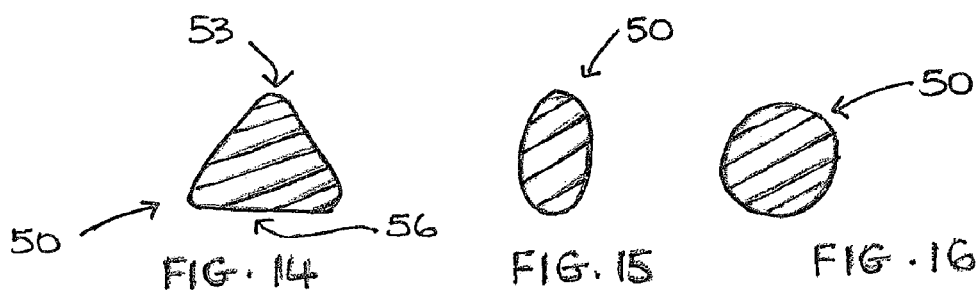
FIG. 14 is a cross-sectional view of a transannular band with a triangular cross-section.
FIG. 15 is a cross-sectional view of a transannular band with an oblong cross-section.
FIG. 16 is a cross-sectional view of a transannular band with a circular cross-section.
Figure 17:
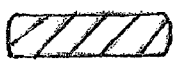
FIG. 17 is a cross-sectional view of a transannular band with a rectangular cross-section.

The central portion of the transannular band 50 can have a variety of cross-sectional shapes, as illustrated in FIGS. 14-17. For example, the cross sectional shape can be substantially rectangular, circular, oblong or triangular. The edges of the transannular band 50 can be rounded or otherwise configured so that the transannular band 50 presents an atraumatic surface 51 to the valve leaflets. In some embodiments, the cross-section can be oriented in a particular fashion to enhance performance of the transannular band 50. For example as shown in FIG. 14, a transannular band 50 with a triangular cross section can be designed so that a relatively larger surface 56 of the triangle contacts the valve leaflets while a lower profile leading edge 53 of the triangle opposite the surface 51 faces the left atrium. This configuration allows a larger surface area to make contact with and support the mitral valve leaflets, while also presenting a more streamlined shape that provides less resistance to blood flowing from the left atrium to the left ventricle. Decreasing the resistance to blood flow is desirable because it can reduce turbulence and reduce the impedance of the transannular band 50 on the filling of the left ventricle. Similarly, the transannular bands 50 with an oblong or rectangular cross-section can be oriented to either increase the surface area for contact with the valve leaflets, or be oriented to reduce the resistance to blood flow.

The dimensions of the transannular band 50 will vary, depending upon the specific configuration of the band 50 as well as the intended patient. In general, transannular band 50 will have an axial length from first end 52 to second end 54 within the range of from about 20 mm to about 32 mm. In one embodiment, intended for a typical male adult, the axial length of the transannular band 50 is about 24 mm to 26 mm. The width of the transannular band 50 in the central zone 64 may be varied depending upon the desired performance, as will be discussed herein. In general, the trailing surface 51 against which leaflets will seat is preferably large enough to minimize the risk of erosion resulting from repeated contact between the closed leaflets and the implant. The width of the leading edge 53 is preferably minimized, as discussed above, to minimize flow turbulence and flow obstruction. In general, widths of the surface 51 measured perpendicular to the flow of blood are presently contemplated to be less than about 5 mm, and often within the range of from about 5 mm to about 10 mm in the zone of coaptation.

Figure 18:
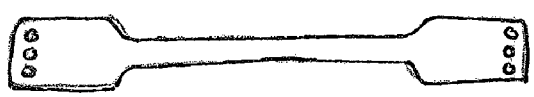
FIG. 18 is a top view of another embodiment of a transannular band.

In some embodiments as illustrated in FIG. 18, the central portion 64 of the transannular band 50 can be narrower in width, measured perpendicular to blood flow than the first and second anchoring portions 58 and 60. By narrowing the central portion 64, the resistance to blood flow can be reduced. However, narrowing the central portion 64 reduces the surface area of the leaflet contact surface 56 that supports the valve leaflets.

In the embodiment illustrated in FIG. 18, the narrowed central portion 64 is separated from the first anchoring portion 58 and second anchoring portion 60 by a first shoulder 57 and second shoulder 59. The length of the central portion 64, between first shoulder 57 and second shoulder 59 can be less than about 50% of the overall length of the device, or less than about 30% of the overall length of the device if it is desired to minimize the obstruction in the center of the flow path, while presenting a wider transverse surface for supporting the leaflets when the valve is closed. Alternatively, the length of the central zone 64 may be greater than 50%, and in some embodiments greater than 75% of the overall length of the implant.

In some embodiments as illustrated in FIGS. 19A, 19B, 21 and 23, a coaptive edge support portion 66 of the central portion 64 of the transannular band 50 can be wider than the adjacent portions of the transannular band 50, leading up to and potentially including the first and second anchoring portions 58 and 60. By increasing the width and surface area of the coaptive edge support portion 66, more support can be provided to the valve leaflets at the coaptive edge. This increased support can increase the width of leaflet coaption. The other portions of the central portion 64 can remain narrow to reduce the resistance to blood flow. The support portion 66 can be located at a fixed position or adjustable along the transannular band so that its position can be optimized by the surgeon and then secured at a fixed point such as by suturing, or removed if deemed unnecessary.

In one implementation of the invention, the transannular band comprises a first component for primary reduction and a second component for fine adjustment. For example, the device illustrated in FIG. 19A may be provided with an adjustable (e.g. slidable) support portion 66. The transannular band may be positioned across the annulus as has been described herein, and hemodynamic function of the valve may be evaluated. The support portion 66 may thereafter be adjusted along the length of the transannular band to treat residual leakage or otherwise optimize the functionality of the implant such as by increasing the zone of coaptation. The second component (e.g. support portion 66) may thereafter be fixed with respect to the transannular band such as by sutures, clips, adhesives, or other techniques known in the art. Alternatively, the second portion may be separate from and connectable to the transannular band such as stitching, clips, suturing or other technique known in the art.

In addition, the coaptive edge support portion 66 can be offset from the center of the transannular band 50, to reflect the asymmetry between the anterior leaflet and the posterior leaflet. For example, the coaptive edge support portion 66 can be positioned closer to the first anchoring portion 58 than to the second anchoring portion 60. In certain embodiments, the edge support portion 66 will be centered about a point which is within the range of from about 20% to about 45% of the overall length of the implant from the closest end.

Figure 20:
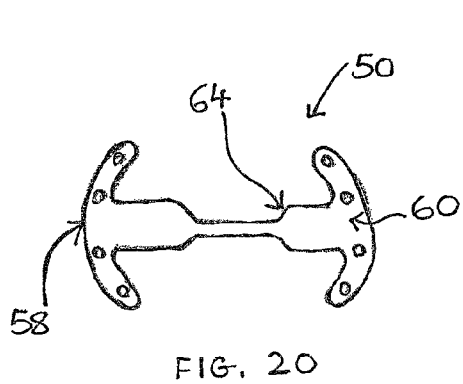
FIGS. 20-23 are top views of other embodiments of a transannular band.

FIG. 20 illustrates another embodiment of a transannular band 50 that is a modification of the transannular band 50 shown in FIG. 18. As illustrated in FIG. 20, the transannular band 50 has a narrow central portion 64 that provides relatively low resistance to blood flow. However, the first and second anchoring portions 58 and 60 extend further in a lateral direction, and can be arcuate to conform to the mitral valve annulus. These laterally extended anchoring portions 58 and 60 provide additional anchoring of the transannular band 50 and can help improve the stability of the device after implantation. The laterally extending anchoring portion 58 and 60 may be provided with any of a variety of structures for facilitating anchoring to the valve annulus. For example, they may be provided with a plurality of apertures 61, for conventional stitching or to receive any of a variety of clips or tissue anchors. The anchoring portions may alternatively be provided with any of a variety of barbs or hooks, or may be provided with a fabric covering such as a Dacron sleeve to facilitate sewing. Measured in the circumferential direction (transverse to the longitudinal axis of the implant 50) the laterally extending anchoring portions will have an arc length of greater than about 5 mm, and, in some embodiments, greater than about 1 cm. Arc lengths of at least about 2 cm, and, in some embodiments, at least about 3 cm may be utilized, depending upon the desired clinical performance.

Figure 21:
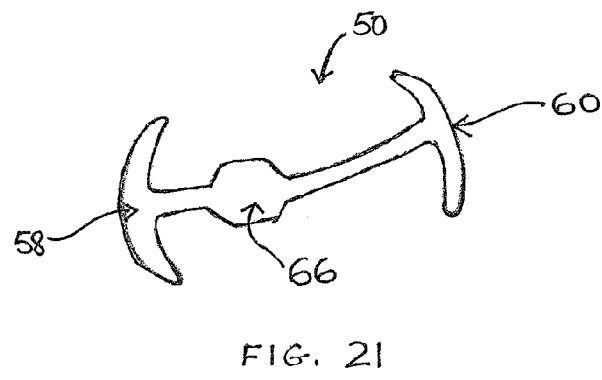

FIG. 21 illustrates another embodiment of a transannular band 50 with the extended anchoring portions 58 and 60 and a wider, offset coaptive edge support portion 66. This embodiment has the benefit of additional stability provided by the extended anchoring portions 58 and 60 and enhanced support of the coaptive edge.

Figure 23:
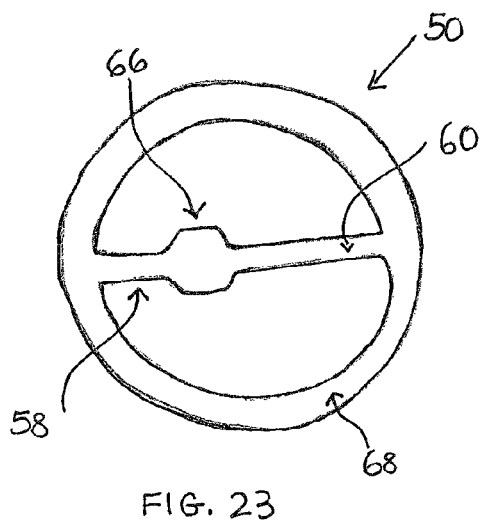
Figure 22:
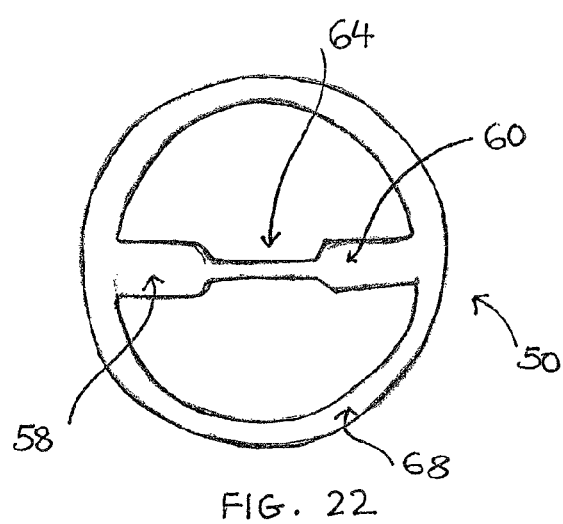

FIGS. 22 and 23 illustrate another embodiment of a transannular band 50 which is combined with an annular ring 68. The annular ring 68 can be used as both a support for the transannular band 50 and, if desired, also to help stabilize the size and shape of the mitral valve annulus itself. In some embodiments, the annular ring 68 can be used to reduce the size of the mitral valve annulus and to bring the mitral valve leaflets closer together. This can be accomplished by, for example, suturing the mitral valve annulus to an annular ring 68 of smaller diameter. In addition, the annular ring 68 provides additional support and stability to the transannular band 50. The anchoring portions 58 and 60 of the transannular band 50 can be formed integrally with the annular ring 68, or the anchoring portions 58 and 60 can be attached to the annular ring by a variety of means, such as suturing, bonding, adhesives, stapling and fusing. FIG. 22 discloses an embodiment with a narrow central portion 64 while FIG. 23 discloses an embodiment with a wider, offset coaptive edge support portion 66.

Figure 23A:
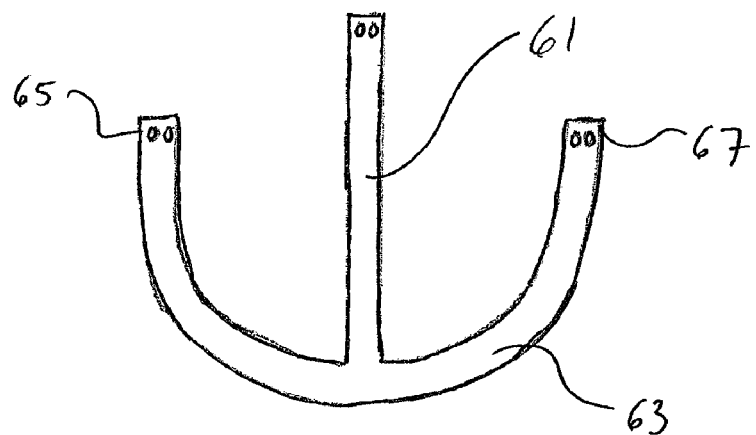
FIG. 23A shows a central mitral transannular band with posterior annuloplasty ring.

FIG. 23A illustrates a further implementation of the invention, adapted to treat ischemic mitral regurgitation with posterior annuloplasty. A transannular band 61 is provided for spanning the leaflet coaption plane as has been described herein. Any of the features described in connection with other transannular bands disclosed herein may be incorporated into the transannular band 61.

An arcuate posterior annuloplasty support 63 is connected to the transannular band 61, and adapted to extend for an arc length along the native annulus. In the illustrated embodiment, the support 63 extends through an arc of approximately 180°, extending from a first trigone attachment zone 65 to a second trigone attachment zone 67. The attachment zones may be provided with sewing apertures, a fabric covering, or other structure for facilitating attachment to tissue. In general, the transannular band 61 will have dimensions similar to those described elsewhere herein. The transverse dimension from first trigone zone 65 to second trigone zone 67 may be varied depending upon the size of the native annulus, but will generally be within the range of from about 35 mm to about 45 mm.

Figure 23B:
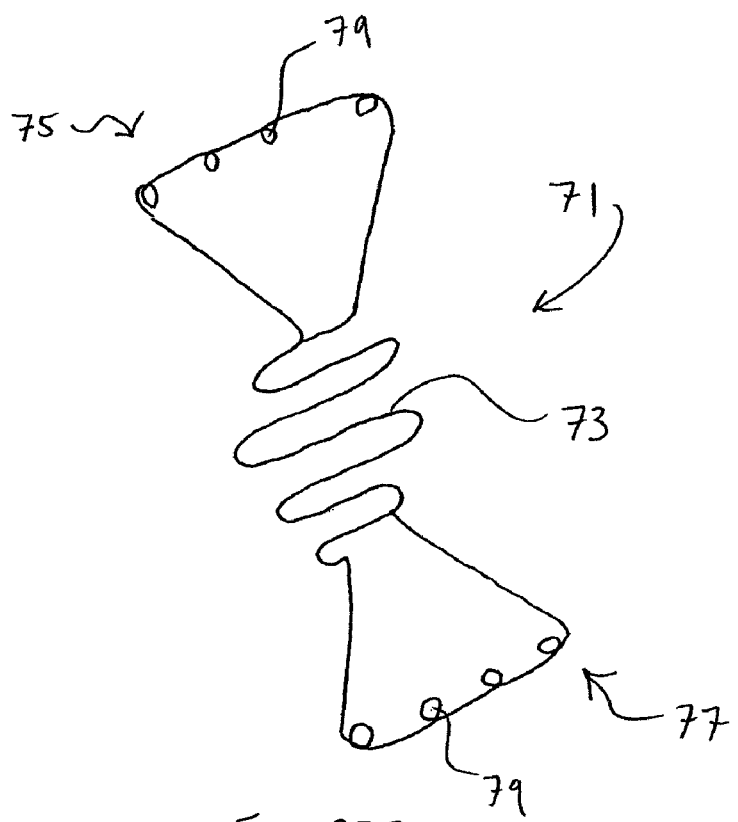
FIG. 23B shows an intraannular band formed from a length of wire.

Referring to FIG. 23B, there is illustrated a transannular band in accordance with the present invention, formed from a single length or several lengths of flexible wire. The bend angles and orientation of the struts in the illustrated embodiment may be readily altered, to accommodate the desired axes of compression which may be desirable for a particular deployment procedure.

In general, the transannular band 71 comprises an elongate flexible wire 73 formed into a serpentine pattern, for providing a support for the valve leaflets as has been discussed herein. Although not illustrated in FIG. 23B, the wire 73 may be formed such that it bows or inclines in the direction of the ventricle to achieve early closure as is discussed elsewhere herein. The wire 73 may extend into a first connection section 75 and a second connection section 77. Each of the connection sections 75 and 77 may be provided with a plurality of eyelets 79, to receive sutures for attaching the implant to the valve annulus. The implant may be formed from any of a variety of flexible materials, including various polymers described elsewhere herein as well as Nitinol, stainless steel or other metals known in the art. This design has an advantage of providing a relatively large support footprint against the valve leaflets, while at the same time optimizing the area of open space to permit maximum blood flow therethrough.

FIGS. 24-27 illustrate side views of transannular bands 50 with different inclinations. One of the objectives of the present invention is to not merely provide support to the leaflets during systole, but to elevate the plane of coaption in the direction of the ventricle, to cause early coaption (closure) relative to the cardiac cycle, as is discussed elsewhere herein. The variation in conditions, and other patient to patient variations may warrant production of the transannular band of the present invention in an array of sizes and/or configurations, so that clinical judgment may be exercised to select the appropriate implant for a given case. Alternatively, the transannular band may be provided in an adjustable form or a modular form so that an implant of the desired configuration can be constructed or modified intraoperatively at the clinical site. In a three segment embodiment, such as that illustrated in FIGS. 24 through 27, a central segment may be provided for positioning within the center of the flow path, or centered on the coaptive edges of the leaflets. First and second end portions may be connected to the central portion, for supporting the central portion relative to the tissue anchors. First and second end portions may be provided in a variety of lengths and curvatures, enabling construction of a relatively customized modular implant as may be desired for a particular patient.

Figure 24:
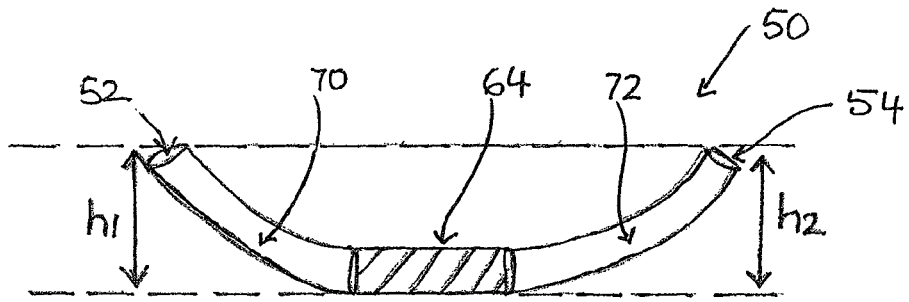
FIGS. 24-27 are side views of other embodiments of a transannular band.

For example, FIG. 24 illustrates a transannular band 50 with a central portion 64 and two gently angled arm portions 70 and 72. The first and second ends 52 and 54 are displaced from the central portion 64 by a height, h1 and h2, respectively. In FIG. 24, h1 and h2 are about equal and can range from about 0 mm to about 10 mm. Preferably h1 and h2 will be at least about 2 mm and will often be at least about 4 mm or 6 mm or more, but generally no more than about 10 mm or 12 mm.

Figure 25:
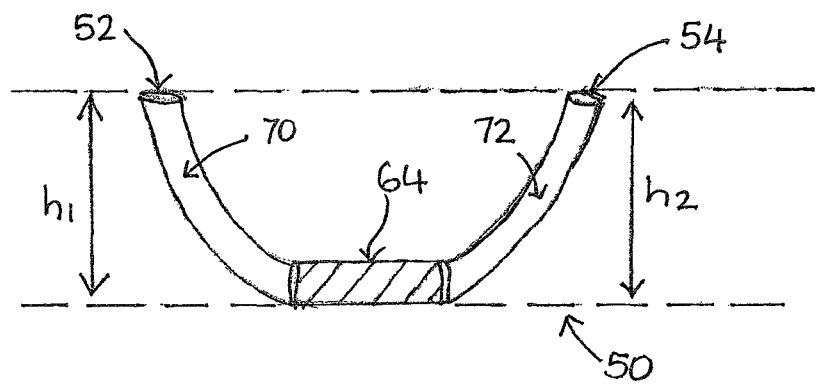
Figure 26:
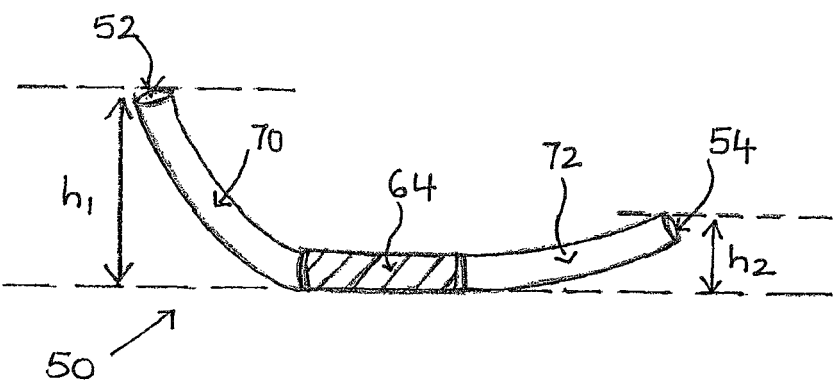
Figure 27:
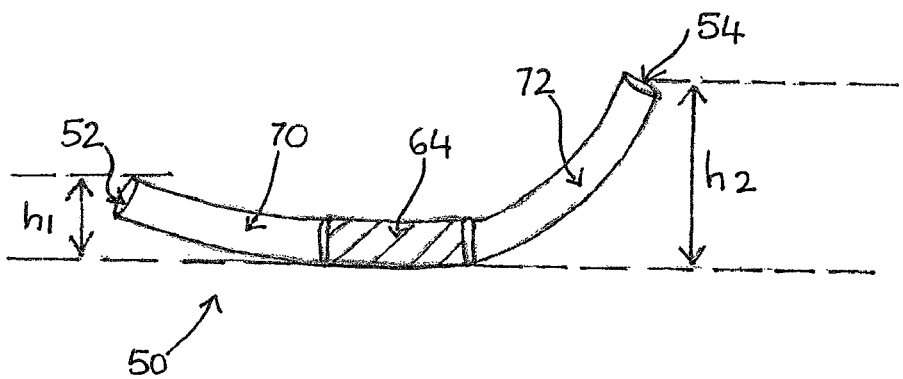

FIG. 25 illustrates a transannular band 50 with a central portion 64 and two sharply angled arm portions 70 and 72. The first and second ends 52 and 54 are displaced from the central portion 64 by a height, h1 and h2, respectively. In FIG. 25, h1 and h2 are about equal and can range from about 8 mm to about 12 mm. FIG. 26 illustrates a transannular band 50 with a central portion 64, a highly angled first arm 70 and a gently angled second arm 72. The first and second ends 52 and 54 are displaced from the central portion 64 by a height, h1 and h2, respectively. In FIG. 26, h1 is greater than h2. h1 ranges from about 6 mm to about 10 mm, while h2 ranges from about 2 mm to about 6 mm. FIG. 27 illustrates a transannular band 50 with a central portion 64, a gently angled first arm 70 and a highly angled second arm 72. The first and second ends 52 and 54 are displaced from the central portion 64 by a height, h1 and h2, respectively. FIG. 27, may be a mirror image of FIG. 26.

The transannular band 50 can be made of any of a variety of materials that are compatible with implantation within a patient's body and which has the requisite structural integrity to support the mitral valve leaflets. For example, suitable materials include titanium, titanium alloys, stainless steel, stainless steel alloys, nitinol, other metals and alloys, ceramics, and polymers such as PTFE, polycarbonate, polypropylene HDPE, PEEK, PEBAX and the like.

In order to reduce the thrombogenicity of the transannular band 50, the transannular band 50 can be provided with a smooth surface. In addition, the transannular band 50 can be coated with a variety of substances to reduce thrombogenicity. For example, the transannular band 50 can be coated with a antithrombogenic agent such as heparin, a polymer such as PTFE, or a polymer conjugated with heparin or another antithrombogenic agent.

As illustrated in FIGS. 28-31, the transannular band 50 is implanted in the plane of the mitral valve annulus 28 in a patient suffering from anterior leaflet 26 prolapse caused by the rupture 42 of the chordae tendineae 30 attached to the anterior leaflet 26. Although a prolapsed anterior leaflet 26 is illustrated, it should be understood that the method described herein is also applicable for treating other types of prolapse, such as posterior leaflet prolapse and prolapse caused by elongated leaflets 24 and 26. The transannular band 50 can be attached to the annulus 28 by a variety of techniques, such as sutures, anchors, barbs, stapes, self-expanding stents, or other techniques that are known or are apparent to those of skill in the art.

Figure 29:
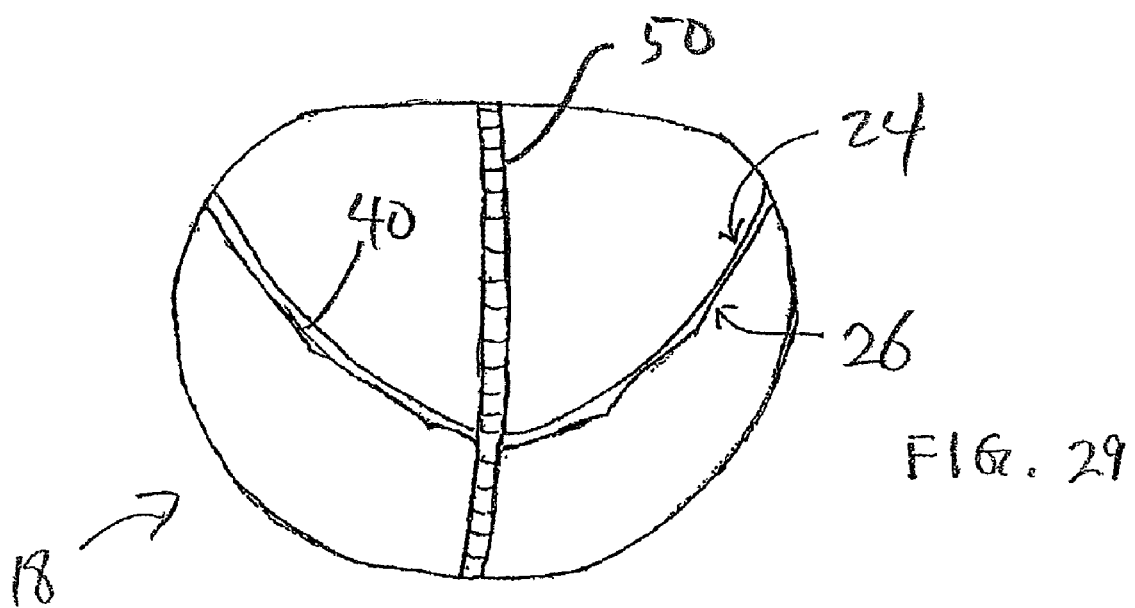
FIG. 29 is a bottom view of the mitral valve of FIG. 28 during systole with a transannular band implanted in the mitral annulus looking from the left atrium to the left ventricle.
Figure 32:
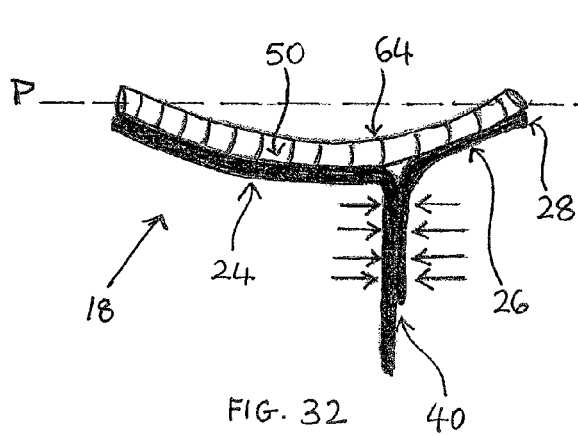
FIG. 32 is a cross-sectional schematic view of the mitral valve of FIG. 28 during systole with a transannular band implanted in the mitral annulus.

As best illustrated in FIGS. 29 and 31, the transannular band 50 is oriented in the annulus 28 so that the transannular band 50 is positioned approximately transversely to the coaptive edge 42 formed by the closure of the mitral valve leaflets 24 and 26. The transannular band 50 can also be positioned over the prolapsed portion of the anterior leaflet 26 so that the transannular band 50 can directly support the prolapsed portion of the anterior leaflet 24 and keep the anterior leaflet 24 above the plane of the mitral valve annulus 28, i.e., elevated in the direction of the ventricle, thereby preventing or reducing prolapse and mitral regurgitation.

Figure 28:
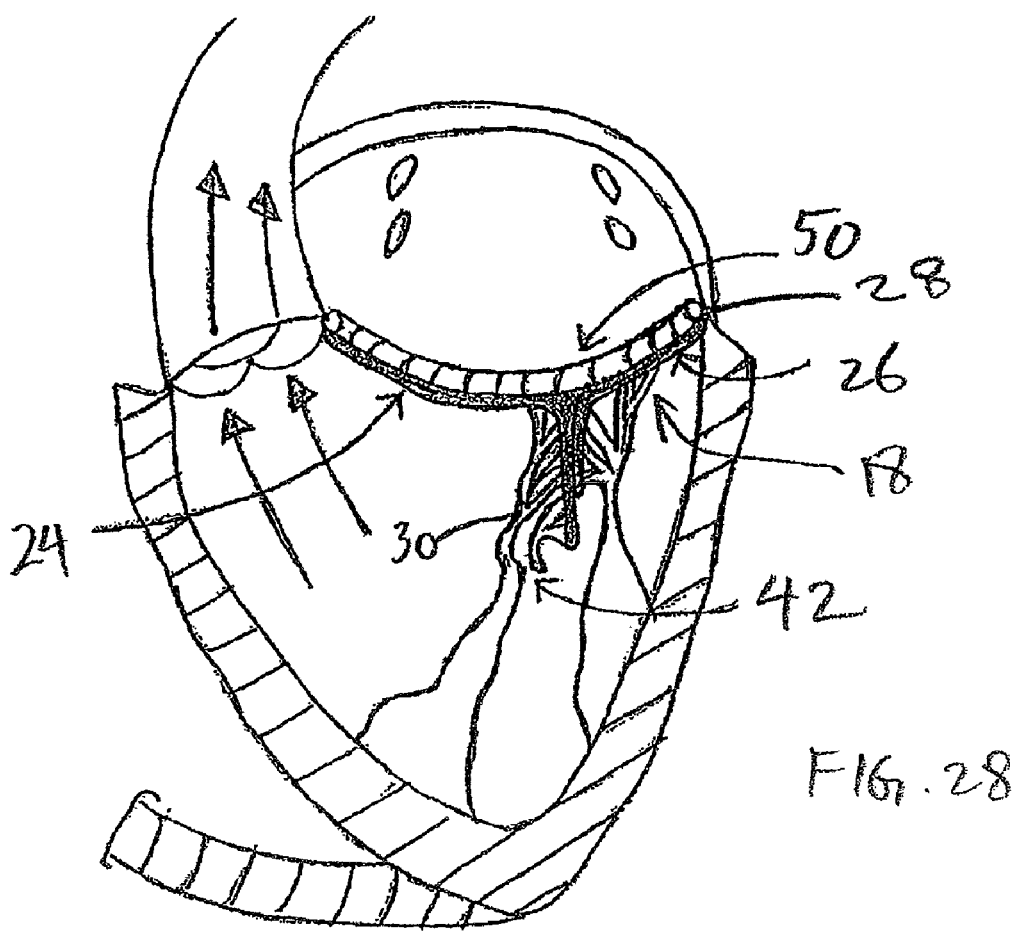
FIG. 28 is a cross-sectional view of a heart during systole with a transannular band implanted in the mitral annulus.

FIGS. 28 and 29 illustrate the effect of the transannular band 50 on the mitral valve 18 during systole. As shown, both the anterior leaflet 24 and the posterior leaflet 26 are supported by the transannular band during closure of the mitral valve 18. The arcuate transannular band 50 functions to keep both leaflets 24 and 26 above the plane of the annulus 28 and enables the leaflets 24 and 26 to form a coaptive edge 40. Although a single transannular band 50 has been illustrated, in some embodiments, multiple transannular bands 50 such as two or three or more can be implanted across the annulus 28 to provide additional support to the mitral valve leaflets 24 and 26.

FIGS. 30 and 31 illustrate the effect of the transannular band 50 on the mitral valve 18 during diastole. During diastole, the mitral valve 18 opens so that blood can fill the left ventricle 16 from the left atrium 12. As best illustrated in FIG. 31, the transannular band 50 obstructs only a small portion of the mitral valve 18 opening, and therefore, does not cause excessive resistance to blood flow.

Figure 33:
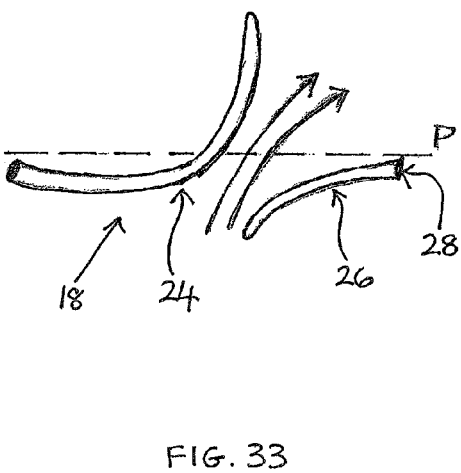
FIG. 33 is a cross-sectional schematic view of the mitral valve of FIG. 32 during systole without the transannular band implanted in the mitral annulus.
Figure 34:
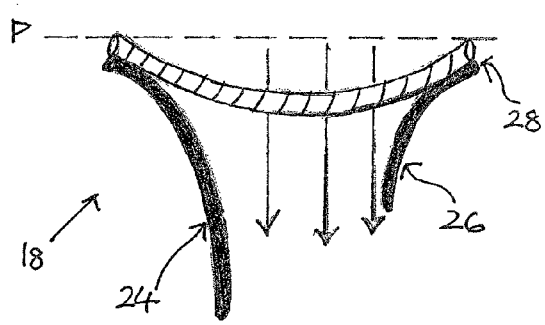
FIG. 34 is a cross-sectional schematic view of the mitral valve of FIG. 30 during diastole with the transannular band implanted in the mitral annulus.
Figure 35:
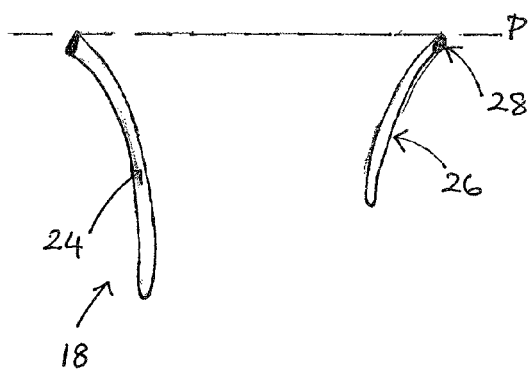
FIG. 35 is a cross-sectional schematic view of the mitral valve of FIG. 34 during diastole without the transannular band implanted in the mitral annulus.

FIGS. 32-35 are cross-sectional side views of the mitral valve 18 with and without the support of the transannular band 50. During systole, the mitral valve 18 closes. Without the transannular band 50, the anterior leaflet 24 crosses the plane P defined by the mitral valve annulus 28 and prolapses, which leads to mitral regurgitation, as shown in FIG. 33. However, by implanting the transannular band 50 in the annulus 28 such that the arcuate transannular band 50 arches towards the left ventricle and the central portion 64 is displaced from the plane P, the anterior leaflet 24 is prevented from prolapsing above the plane P thus eliminating or reducing retrograde flow (shown in FIG. 33). The leaflets 24 and 26 rest upon the transannular band 50 and the pressure exerted by the blood upon the distal portion of the leaflets 24 and 26 form the coaptive edge 40. As illustrated in FIGS. 34 and 35, the performance of the mitral valve 18 during diastole is not substantially affected by the transannular band 50.

Figure 36:
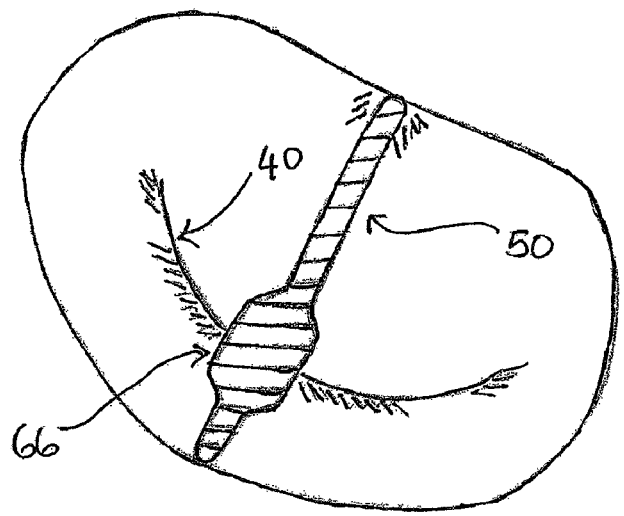
FIG. 36 is a bottom view of the mitral valve during systole with another embodiment of the transannular band implanted in the mitral annulus looking from the left atrium to the left ventricle.
Figure 38:
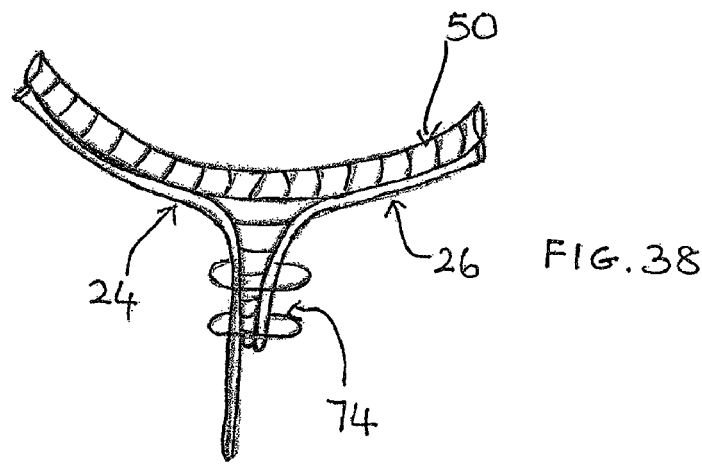
FIG. 38 is a cross-sectional schematic view of the mitral valve treated with the transannular band of FIG. 37 and an Alfieri type procedure.

Although the method of implanting and positioning the transannular band 50 has been illustrated with one embodiment of the transannular band 50, other embodiments as described above can also be used. For example, FIG. 36 illustrates a transannular band 50 with a wider, offset coaptive edge support portion 66 that has been implanted in the mitral valve annulus. As shown, the coaptive edge support 66 is offset so that it positioned to support the coaptive edge of the mitral valve 18. In addition, the transannular band 50 can be used in conjunction with other devices and procedures, such as a separate or integrally attached annular or annuloplasty ring described above. In addition, the transannular band 50 can be used in conjunction with the Alfieri procedure, where the tips of the mitral valve leaflets 24 and 26 are sutured 74 together, as shown in FIG. 38.

Figure 37:
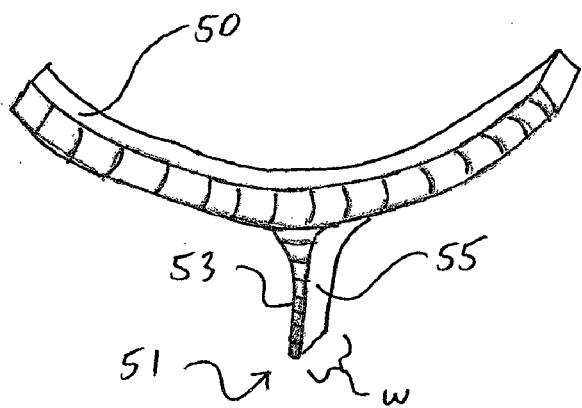
FIG. 37 is a cross-sectional view of a transannular band with a transverse leaflet support.

Referring to FIG. 37, there is illustrated a perspective view of a transannular band 50 having a transverse projection or support 51 extending in the direction of the ventricle. The support 51 has a width W, which may be at least about 3 mm, and in some embodiments, at least about 5 mm, and in other embodiments at least about 1.0 cm. The projection 51 may be utilized without an Alfieri stitch, so that the leaflets of the mitral valve close against opposing side walls 53 and 55 of the projection 51. The projection 51 thus helps center the closure of the leaflets, as well as controlling the width of coaption. In addition, the band 50 is illustrated as convex in the direction of the ventricle, to accomplish early closure as has been discussed herein.

The transannular band 50 can be implanted via an open surgical procedure, or alternatively, via a percutaneous procedure using a translumenally implantable embodiment. In the translumenally implantable embodiment, one or more transannular bands can be attached to a self-expandable support structure, such as a self-expandable ring or self-expandable stent having a relatively short axial length relative to its expanded diameter. The transannular band and the compressed self-expandable support structure are loaded into a catheter with a retractable outer sheath which is inserted percutaneously and advanced translumenally into or across the mitral valve. The retractable outer sheath can be retracted to allow the self-expandable support structure to expand against the annulus, thereby positioning the one or more transannular bands in about the plane of the mitral annulus. Each transannular band can be characterized by a longitudinal axis, and the transannular band is orient in the mitral valve such that the longitudinal axis of the transannular band in oriented transversely to the coaptive edge of the mitral valve.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

What is claimed is:

1. A method of treating a mitral valve, the method comprising:
implanting in the mitral annulus an intraannular band comprising an elongate body having a first end, a first anchoring portion located proximate the first end, a second end, a second anchoring portion located proximate the second end, and a central portion, wherein the central portion has a convex arcuate shape, the central portion displaced out of an intraannular plane of the mitral valve, said plane containing the first end and the second end;
attaching the first anchoring portion to a first portion of the mitral annulus; and
attaching the second anchoring portion to a second portion of the mitral annulus such that the intraannular band extends transversely across coaptive edges formed by the closure of the mitral valve leaflets during systole and the central portion is convex in the direction of the left ventricle relative to the first anchoring portion and the second anchoring portion to elevate the position of the coaptive edges in the direction of the ventricle during valve closure and thereby cause early coaption relative to the cardiac cycle,
wherein the coaptive edges of the leaflets are unsupported by the band during diastole, and
wherein attaching the first and second anchoring portions does not affect the size and shape of the mitral annulus.

2. A method of treating a mitral valve as in claim 1, wherein the first anchoring portion comprises an arcuate shape.

3. A method of treating a mitral valve as in claim 2, wherein the first anchoring portion extends around a portion of the circumference of the mitral annulus.

4. A method of treating a mitral valve as in claim 3, wherein the second anchoring portion extends around a portion of the circumference of the mitral annulus.

5. A method of treating a mitral valve as in claim 3, wherein the first anchoring portion has an arc length of greater than about 5 mm.

6. A method of treating a mitral valve as in claim 5, wherein the first anchoring portion has an arc length of greater than about 1 cm.

7. A method of treating a mitral valve as in claim 5, wherein the first anchoring portion has an arc length of greater than about 2 cm.

8. A method of treating a mitral valve as in claim 1, wherein the second anchoring portion comprises an arcuate shape.

9. A method of treating a mitral valve as in claim 1, wherein the central portion comprises a narrowed portion configured to reduce resistance to blood flow.

10. A method of treating a mitral valve as in claim 1, wherein the method treats mitral valve prolapse.

11. A method of treating a mitral valve as in claim 1, wherein the method treats mitral valve regurgitation.

12. A method of treating a mitral valve as in claim 1, wherein the central portion is narrower than that of the first anchoring portion and the second anchoring portion.

13. A method of treating a mitral valve as in claim 1, wherein the first anchoring portion comprises a plurality of apertures.

14. A method of treating a mitral valve as in claim 1, wherein attaching the first anchoring portion to a first portion of the mitral annulus comprises suturing the first anchoring portion to the first portion of the mitral annulus.

15. A method of treating a mitral valve as in claim 1, wherein attaching the second anchoring portion to a second portion of the mitral annulus comprises suturing the second anchoring portion to the second portion of the mitral annulus.

16. A method of moving mitral valve leaflet coaption to an earlier point in the cardiac cycle, comprising the steps of:
providing an intraannular, transvalvular band dimensioned for attachment within a plane of the mitral valve annulus, wherein the band comprises an elongate body having a first end, a second end, and a central portion having a convex arcuate shape, wherein the band does not comprise an annuloplasty ring;
attaching the band within the plane of the annulus such that the arcuate shaped portion of the band extends transversely across coaptive edges formed by the mitral valve leaflets and is convex in the direction of the ventricular side of the plane to support the leaflets and elevate the position of the coaptive edges in the direction of the ventricle during valve closure,
wherein the coaptive edges of the leaflets are unsupported by the band during diastole.

17. A method of moving mitral valve leaflet coaption as in claim 16, wherein the elevate the position step comprises elevating the position of the coaptive edges by at least about 4 mm.

18. A method of moving mitral valve leaflet coaption as in claim 16, wherein the elevate the position step comprises elevating the position of the coaptive edges by an amount within the range of from about 6 mm to about 12 mm.

19. A method of treating a mitral valve as in claim 16, wherein the position of the coaptive edges is elevated by at least about 4 mm.

20. A method of treating a mitral valve as in claim 16, wherein the position of the coaptive edges is elevated by an amount within the range of about 6 mm to about 12 mm.

21. A method of moving mitral valve leaflet coaption to an earlier point in the cardiac cycle, comprising the steps of:
providing an intraannular, transvalvular band dimensioned for attachment within a plane of the mitral valve annulus, wherein the band comprises an elongate body having a first end, a second end, and an arcuate central portion;
attaching the band within the plane of the annulus such that the arcuate shaped portion of the band extends transversely across coaptive edges formed by the mitral valve leaflets and extends into the ventricular side of the plane to support the leaflets and elevate the position of the coaptive edges in the direction of the ventricle during valve closure,
wherein the coaptive edges of the leaflets are unsupported by the band during diastole, and
wherein attachment of the band does not affect the size and shape of the mitral valve annulus.

* * * * *